US010437159B2

(12) United States Patent
Tukker et al.

(10) Patent No.: US 10,437,159 B2
(45) Date of Patent: Oct. 8, 2019

(54) MEASUREMENT SYSTEM, LITHOGRAPHIC SYSTEM, AND METHOD OF MEASURING A TARGET

(71) Applicant: ASML Netherlands B.V., Veldhoven (NL)

(72) Inventors: Teunis Willem Tukker, Eindhoven (NL); Gerbrand Van Der Zouw, Waalre (NL); Amandev Singh, Eindhoven (NL)

(73) Assignee: ASML Netherlands B.V., Veldhoven (NL)

(*) Notice: Subject to any disclaimer, the term of this patent is extended or adjusted under 35 U.S.C. 154(b) by 28 days.

(21) Appl. No.: 15/802,701

(22) Filed: Nov. 3, 2017

(65) Prior Publication Data

US 2018/0164699 A1 Jun. 14, 2018

(30) Foreign Application Priority Data

Nov. 10, 2016 (EP) .................................. 16198200

(51) Int. Cl.
*G01N 21/95* (2006.01)
*G03F 7/20* (2006.01)
(Continued)

(52) U.S. Cl.
CPC ... *G03F 7/70633* (2013.01); *G01N 21/95607* (2013.01); *G03F 7/7015* (2013.01);
(Continued)

(58) Field of Classification Search
CPC ............ G01N 21/956; G01N 21/9501; G01N 21/8806; G01N 21/4788;
(Continued)

(56) References Cited

U.S. PATENT DOCUMENTS

2011/0027704 A1 2/2011 Cramer et al.
2011/0043791 A1 2/2011 Smilde et al.
(Continued)

FOREIGN PATENT DOCUMENTS

DE 102014002514 A1 8/2015
WO WO 2009/078708 A1 6/2009
(Continued)

OTHER PUBLICATIONS

International Search Report and Written Opinion of the International Searching Authority directed to related International Patent Application No. PCT/EP2017/077013, dated Feb. 2, 2018; 11 pages.
(Continued)

*Primary Examiner* — Michael P Stafira
(74) *Attorney, Agent, or Firm* — Sterne, Kessler, Goldstein & Fox P.L.L.C.

(57) ABSTRACT

A measurement system is disclosed in which a first optical system splits an input radiation beam into a plurality of components. A modulator receives the plurality of components and applies a modulation to at least one of the components independently of at least one other of the components. A second optical system illuminates a target with the plurality of components and directs radiation scattered by the target to a detection system. The detection system distinguishes between each of one or more components, or between each of one or more groups of components, of the radiation directed to the detection system based on the modulation applied to each component or each group of components by the modulator.

20 Claims, 8 Drawing Sheets

(51) Int. Cl.
*G01N 21/956* (2006.01)
*G03F 9/00* (2006.01)

(52) U.S. Cl.
CPC ........ *G03F 7/70625* (2013.01); *G03F 9/7046* (2013.01); *G03F 9/7069* (2013.01); *G03F 9/7088* (2013.01)

(58) Field of Classification Search
CPC ......... G01N 2021/95676; G01N 21/47; G01N 21/6428; G01N 2201/06113; G01N 2021/6439; G01N 21/95607; G01N 15/1484; G01N 2015/1006; G01N 2015/149; G01N 2021/6463; G01N 21/648; G01N 2201/08; G01N 33/48721; G01N 15/1404; G01N 15/1434; G01N 21/213; G01N 2021/6419; G01N 2021/6421; G01N 2021/8848; G01N 21/33; G01N 21/6402; G01N 21/6408; G01N 21/6452; G01N 21/6454; G01N 21/6486; G01N 21/7746; G01N 2201/0696; G01N 2201/10; G01N 2201/12; G01N 2458/10; G01N 33/54326; G01N 33/54373; G01N 33/5438; G01N 15/10; G01N 15/1429; G01N 15/1459; G01N 15/1463; G01N 2015/0038; G01N 2015/0053; G01N 2015/1081; G01N 2015/1413; G01N 2015/142; G01N 2015/1454; G01N 2021/458; G01N 2021/6482; G01N 2021/655; G01N 2021/7786; G01N 2021/825; G01N 2021/8438; G01N 2021/8845; G01N 21/21; G01N 21/3563; G01N 21/45; G01N 21/4785; G01N 21/554; G01N 21/7703; G01N 21/774; G01N 21/7743; G01N 21/78; G01N 21/8422; G01N 21/88; G01N 21/93; G01N 21/9505; G01N 2201/061; G01N 2201/06146; G01N 2201/062; G01N 2201/0631; G01N 2201/0635; G01N 2201/0638; G01N 2201/0675; G01N 2201/0683; G01N 2201/0686; G01N 2201/0697; G01N 2201/0853; G01N 2201/1296; G01N 2333/5709; G01N 23/20; G01N 27/27; G01N 27/3721; G01N 27/3272; G01N 2800/2814; G01N 2800/2821; G01N 2800/2835; G01N 33/487; G01N 33/5058; G01N 33/5302; G01N 33/5308; G01N 33/54306; G01N 33/558; G01N 33/6896; G01B 11/272; G01B 2210/56; G01B 11/24; G01B 11/00; G01B 11/002; G01B 11/30; G01B 11/02; G01B 11/028; G01B 11/06; G01B 11/14; G01B 11/26; G01B 11/27; G01B 15/00; G01B 2290/55; G01B 9/02016; G01B 9/02058; G01J 1/08; G01J 1/42; G01J 2001/4247; G01J 2003/2826; G01J 9/00

See application file for complete search history.

(56) References Cited

U.S. PATENT DOCUMENTS

| | | | |
|---|---|---|---|
| 2012/0242970 | A1 | 9/2012 | Smilde et al. |
| 2013/0100427 | A1* | 4/2013 | Koolen .................... G03F 1/42 355/67 |
| 2016/0011523 | A1 | 1/2016 | Singh et al. |
| 2016/0025992 | A1* | 1/2016 | Van Der Zouw ........................... G01N 21/8806 250/216 |
| 2016/0161245 | A1 | 6/2016 | Fu et al. |
| 2017/0059408 | A1 | 3/2017 | Korner et al. |
| 2017/0184977 | A1* | 6/2017 | Jak ......... G01B 11/26 |
| 2018/0004095 | A1 | 1/2018 | Tukker et al. |
| 2018/0059552 | A1 | 3/2018 | Pandey |
| 2018/0341105 | A1* | 11/2018 | Sobolev ............ G01B 9/02058 |

FOREIGN PATENT DOCUMENTS

| | | |
|---|---|---|
| WO | WO 2009/106279 A1 | 9/2009 |
| WO | WO 2018/001747 A1 | 1/2018 |
| WO | WO 2018/036828 A1 | 3/2018 |

OTHER PUBLICATIONS

Gross et al., "Handbook of Optical Systems: Survey of Optical Instruments," vol. 4, 2008; p. 1045.

\* cited by examiner

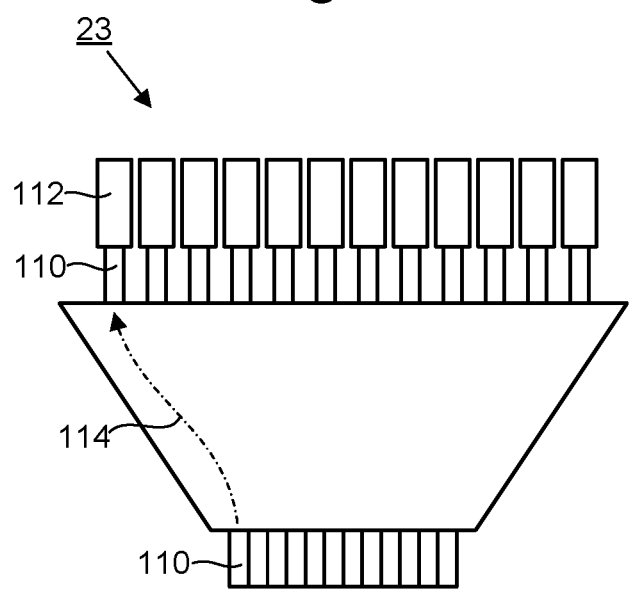

MEASUREMENT SYSTEM, LITHOGRAPHIC SYSTEM, AND METHOD OF MEASURING A TARGET

FIELD

The present invention relates to a measurement system, a lithographic system using the measurement system, and a method of measuring a target.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in patent publications US20110027704A, US20110043791A and US20120242970A. The contents of all these applications are also incorporated herein by reference. Diffraction-based overlay using dark-field detection of the diffraction orders enables overlay measurements on smaller targets. These targets can be smaller than the illumination spot and may be surrounded by product structures on a wafer. Targets can comprise multiple gratings which can be measured in one image.

In the known metrology technique, overlay measurement results are obtained by measuring an overlay target twice under certain conditions, while either rotating the overlay target or changing the illumination mode or imaging mode to obtain separately the $-1^{st}$ and the $+1^{st}$ diffraction order intensities. The intensity asymmetry, a comparison of these diffraction order intensities, for a given overlay target provides a measurement of target asymmetry, that is, asymmetry in the target. This asymmetry in the overlay target can be used as an indicator of overlay error (undesired misalignment of two layers).

Metrology apparatuses, when performing such dark field scatterometry, presently can only perform measurements using measurement radiation of a single wavelength at any one time. However, different targets in different layers may show different behavior to different wavelength measurement radiation, which can result in variable measurement quality. Variations as a function of wavelength may also arise due to processing induced changes to the target structure. For example, semiconductor manufacturing processes such as Chemical Mechanical Planarization etching and non-uniformity of layer thickness variations change the structure of the metrology target and hence also the optimum wavelength. It is therefore desirable for measurement radiation to be individually tuned to a target and/or layer.

SUMMARY

It is desirable to provide apparatus and methods that allow high quality measurements to be performed efficiently.

According to an aspect of the invention, there is provided a measurement system comprising: a first optical system configured to split an input radiation beam into a plurality of components; a modulator configured to receive the plurality of components and apply a modulation to at least one of the components independently of at least one other of the components; and a second optical system configured to illuminate a target with the plurality of components and direct radiation scattered by the target to a detection system, wherein: the detection system is configured to distinguish between each of one or more components, or between each of one or more groups of components, of the radiation directed to the detection system based on the modulation applied to each component or each group of components by the modulator.

According to an aspect of the invention, there is provided a method of measuring a target, comprising: splitting an input radiation beam into a plurality of components; applying a modulation to at least one of the components independently of at least one other of the components; illuminating a target with the plurality of components; detecting radiation scattered by the target; and distinguishing between each of one or more components, or between each of one or more groups of components, of the radiation scattered by the target based on the modulation applied to each component or each group of components.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 11 depicts a detection system comprising a plurality of detectors and a corresponding plurality of optical fibers.

DETAILED DESCRIPTION OF EXEMPLARY EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Figure 1:
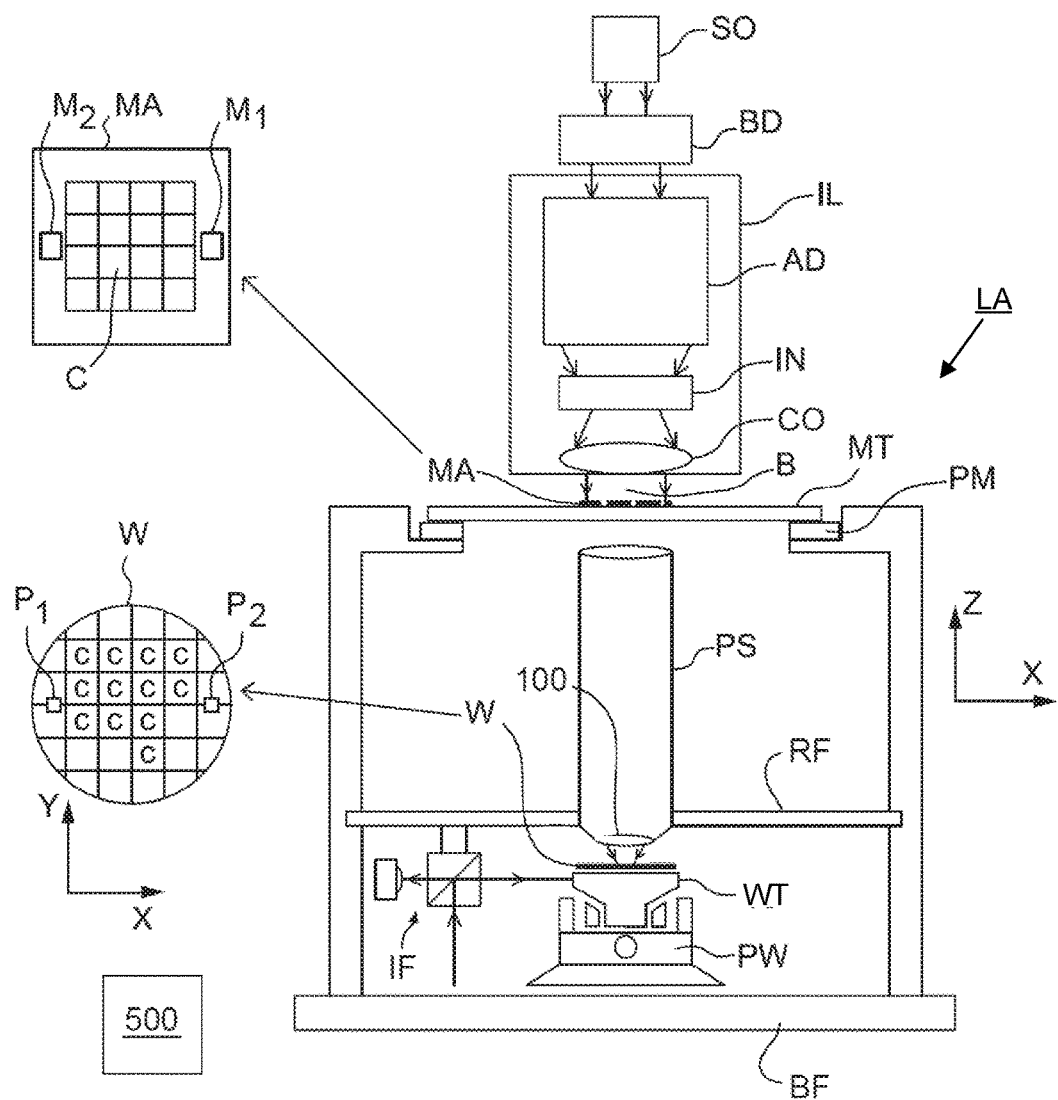
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing various types of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

In this embodiment, for example, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables and, for example, two or more mask tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (which are commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
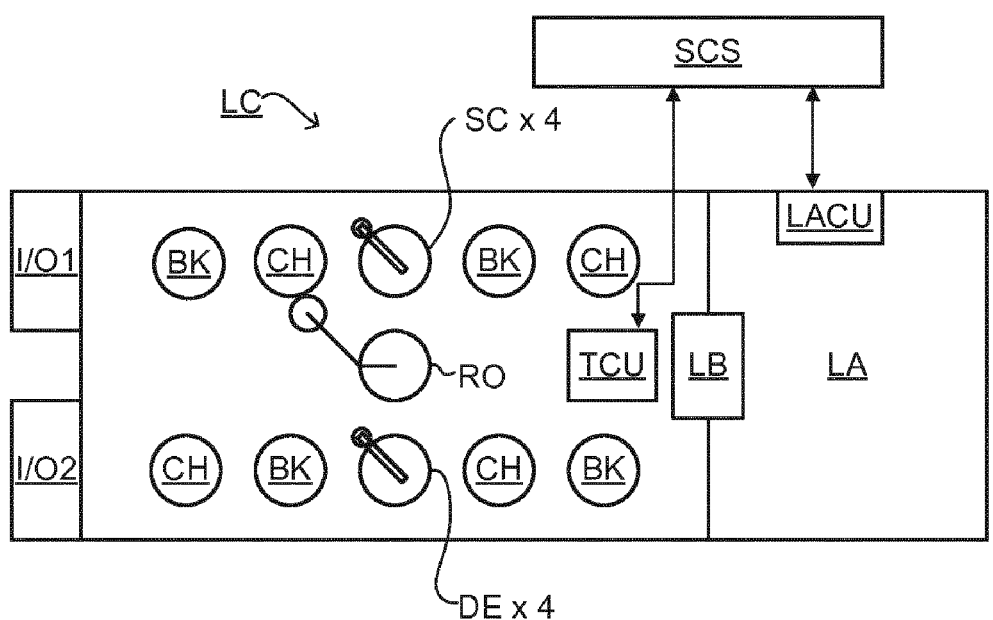
FIG. 2 depicts a lithographic cell or cluster.

As shown in FIG. 2 the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU that is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments, for example, can be made to exposures of subsequent substrates, especially if the inspection can be done soon and fast enough that other substrates of the same batch are still to be exposed. Also, already exposed substrates may be stripped and reworked to improve yield, or possibly be discarded, thereby avoiding performing exposures on substrates that are known to be faulty. In a case where only some target portions of a substrate are faulty, further exposures can be performed only on those target portions that are deemed to be non-faulty.

A metrology apparatus is used to determine the properties of the substrates, and in particular, how the properties of different substrates or different layers of the same substrate vary from layer to layer. The metrology apparatus may be integrated into the lithographic apparatus LA or the lithocell LC or may be a stand-alone device. To enable most rapid measurements, it is desirable that the metrology apparatus measure properties in the exposed resist layer immediately after the exposure. However, the latent image in the resist has a very low contrast, as in there is only a very small difference in refractive index between the parts of the resist which have been exposed to radiation and those which have not—and not all metrology apparatus have sufficient sensitivity to make useful measurements of the latent image. Therefore measurements may be taken after the post-exposure bake step (PEB) that is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

A metrology apparatus is shown in FIG. 3(a). A target T and diffracted rays of measurement radiation used to illuminate the target are illustrated in more detail in FIG. 3(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

Figure 3:
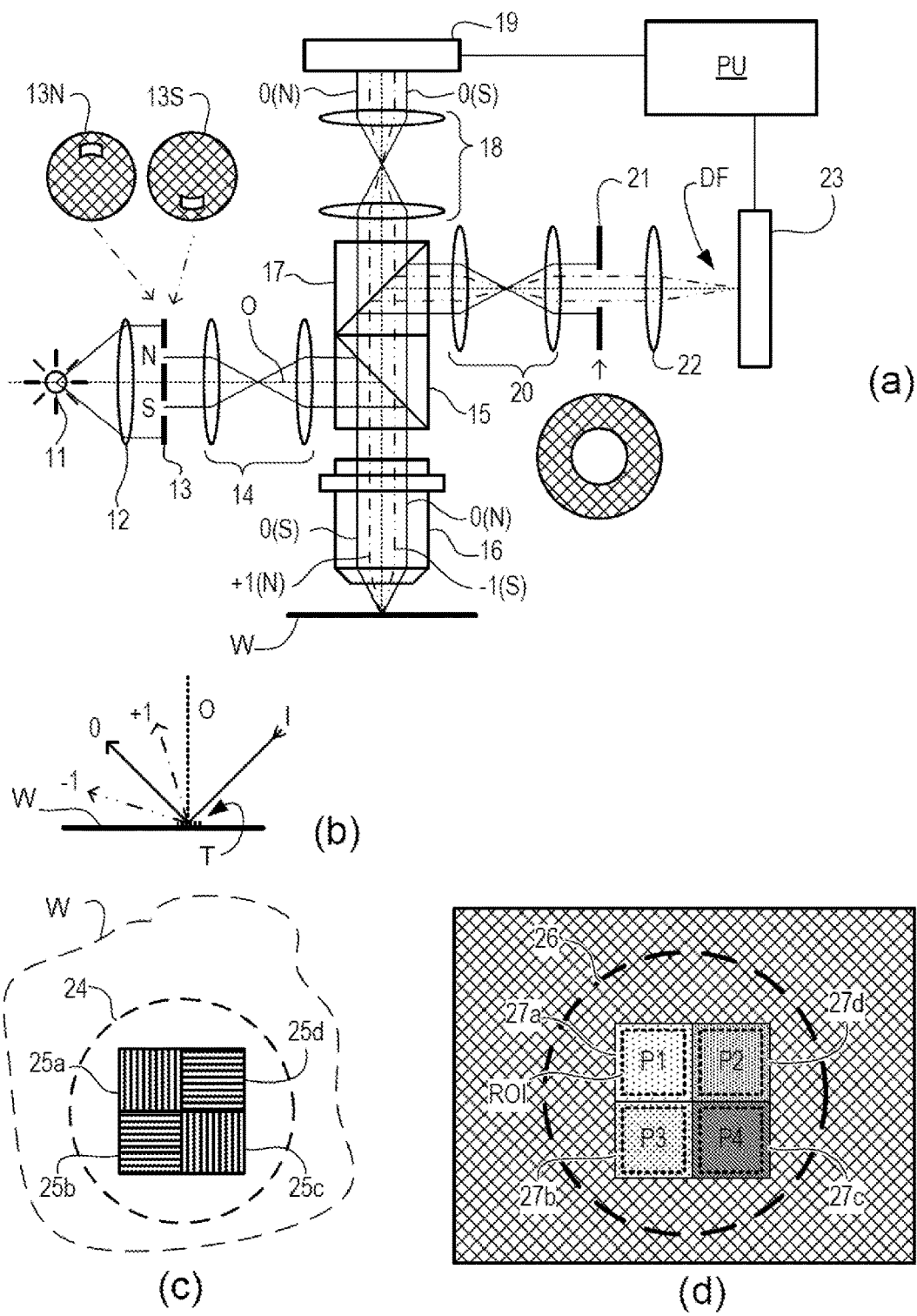
FIG. 3 comprises (a) a schematic diagram of a dark field scatterometer for use in measuring targets using a first pair of illumination apertures; (b) a detail of diffraction spectrum of a target grating for a given direction of illumination; (c) a depiction of a known form of multiple grating target and an outline of a measurement spot on a substrate; and (d) a depiction of an image of the target of FIG. 3(c) obtained in the scatterometer of FIG. 3(a)

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 3) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. The use of these, and numerous other variations and applications of the apparatus are described in prior published applications, mentioned above.

FIG. 3(c) depicts a (composite) target formed on a substrate according to known practice. The target in this example comprises four gratings 25a to 25d positioned closely together so that they will all be within a measurement scene or measurement spot 24 formed by the metrology radiation illumination beam of the metrology apparatus. The four gratings thus are all simultaneously illuminated and simultaneously imaged on sensors 19 and 23. In an example dedicated to measurement of overlay, gratings 25a to 25d are themselves composite gratings formed by overlying gratings that are patterned in different layers of the semi-conductor device formed on substrate W. Gratings 25a to 25d may have differently biased overlay offsets (deliberate mismatch between layers) in order to facilitate measurement of overlay between the layers in which the different parts of the composite gratings are formed. Such techniques are well known to the skilled person and will not be described further. Gratings 25a to 25d may also differ in their orientation, as shown, so as to diffract incoming radiation in X and Y directions. In one example, gratings 25a and 25c are X-direction gratings with biases of the +d, −d, respectively. Gratings 25b and 25d are Y-direction gratings with offsets +d and −d respectively. Separate images of these gratings can be identified in the image captured by sensor 23. This is only one example of a target. A target may comprise more or fewer than four gratings, or only a single grating.

FIG. 3(d) shows an example of an image that may be formed on and detected by the sensor 23, using the target of FIG. 3(c) in the apparatus of FIG. 3(a). While the pupil plane image sensor 19 cannot resolve the different individual gratings 25a to 25d, the image sensor 23 can do so. The dark rectangle represents the field of the image on the sensor, within which the illuminated spot 24 on the substrate is imaged into a corresponding circular area 26. Within this, rectangular areas 27a to 27d represent the images of the small target gratings 25a to 25d. If the targets are located in product areas, product features may also be visible in the periphery of this image field. Image processor and controller PU processes these images using pattern recognition to identify the separate images 27a to 27d of gratings 25a to 25d. In this way, the images do not have to be aligned very precisely at a specific location within the sensor frame, which greatly improves throughput of the measuring apparatus as a whole.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

Presently, when performing dark field measurements using the second imaging branch, the measurement radiation used comprises only a single wavelength. The measurement radiation shows different behavior for different layers of the substrate being measured. Therefore, the wavelength of the measurement radiation should be optimized for the layer in which the target being measured is comprised. This means that the measurement radiation needs individual tuning for different measurements of targets in different layers. This takes significant time, while it is always desirable to reduce measurement time to increase fabrication productivity and/or accuracy (by allowing more measurements to be made). In addition, multilayer overlay measurements are sometimes performed, where multiple targets in different layers are captured in a single image. For such multilayer measurements, optimization of wavelength for targets in different layers is not possible, and the wavelength chosen will only be a best compromise for the different targets.

Figure 4:
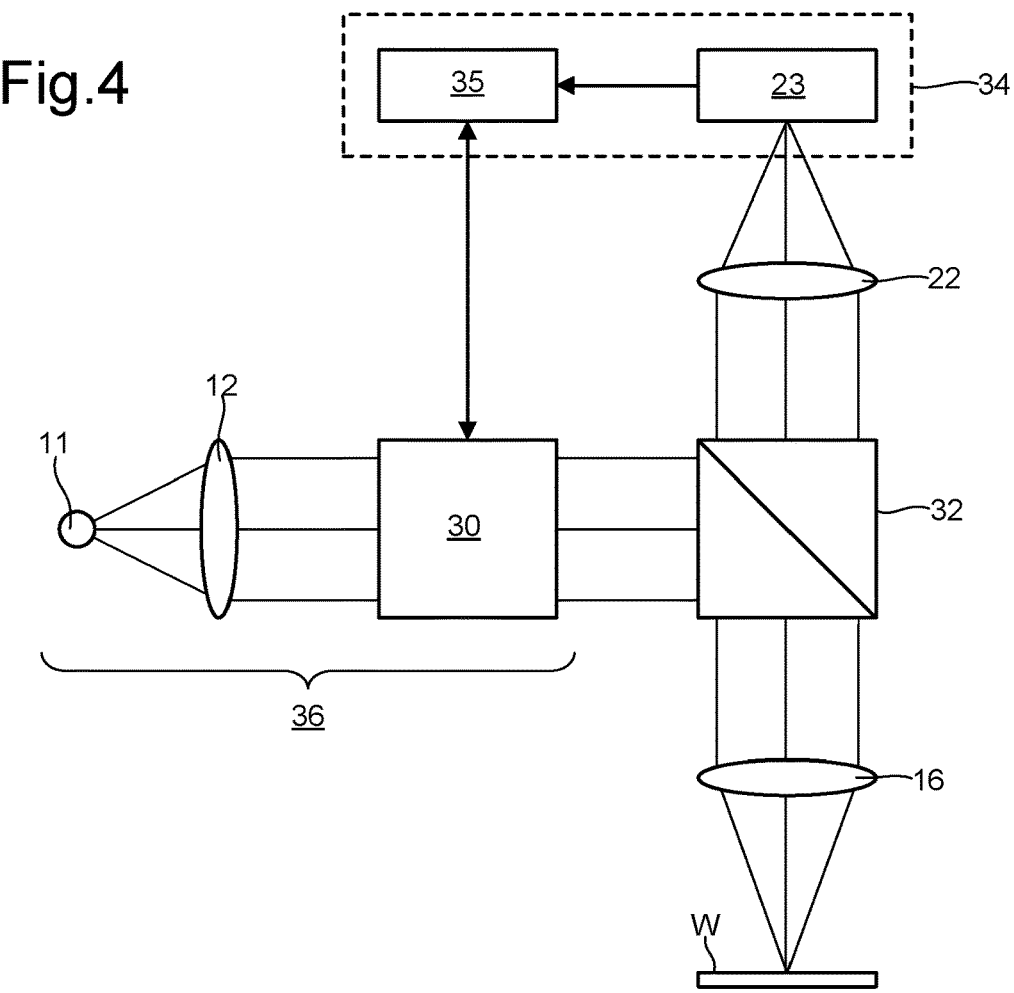
FIG. 4 is a schematic diagram of a measurement system.

FIG. 4 schematically illustrates a measurement system architecture (which may also be referred to as a metrology apparatus, particularly when used to measure targets formed by a lithography process on a substrate) which aims to address these issues. It does this by performing measurements on a target (which may be similar to the target depicted in FIG. 3(c) for example) using multiple wavelengths in parallel. The technique used may be referred to as hyperspectral imaging. This allows selection of the optimal wavelength for each individual layer. Therefore, when performing a multilayer measurement for example, the wavelength can be optimized for each target without sacrificing throughput. Also, the provision of a complete spectral map of a target improves the robustness of the overlay measurement with respect to process variation.

Apart from the hyperspectral imaging, the measurement system may be configured to operate largely in the same way as the metrology apparatus of FIG. 3(a), and in particular the second measurement branch of this apparatus (embodiments according to this disclosure may optionally comprise another measurement branch in a similar manner to that illustrated in FIG. 3(a)). The main difference between earlier designs of metrology apparatus and the measurement system of FIG. 4 is the inclusion of a beam processing apparatus 30 for processing a radiation beam, which will be described in further detail below.

The measurement system of FIG. 4 comprises a source 11. The source 11 provides measurement radiation comprising multiple wavelengths. The measurement radiation may comprise a continuous spectrum or multiple discrete wavelengths (or wavelength bands). In an embodiment, the measurement radiation may comprise multiple wavelengths extending from 400 nm to 900 nm.

Lens 12 receives radiation from the source 11 and provides an input radiation beam to the beam processing apparatus 30. The combination of the source 11, lens 12 and beam processing apparatus 30 may be referred to as a radiation system 36. The beam processing apparatus 30 outputs an output radiation beam to a beam splitter 32. The beam splitter 32 redirects the output radiation beam onto the substrate W. A target on the substrate W is illuminated by the output radiation beam. In an embodiment the target comprises a structure formed on the substrate W by a lithographic process. The four gratings 25a-25d of FIG. 3(c) are examples of structures suitable for measurement by the measurement system. Radiation scattered from the target is directed via the beam splitter 32 and lens 22 to a detection system 34. The detection system 34 comprises a sensor 23 and a processing unit 35. The processing unit 35 controls operation of the beam processing apparatus 30. The processing unit 35 also demodulates an output received from the sensor 23 to extract a signal of interest.

Figure 5:
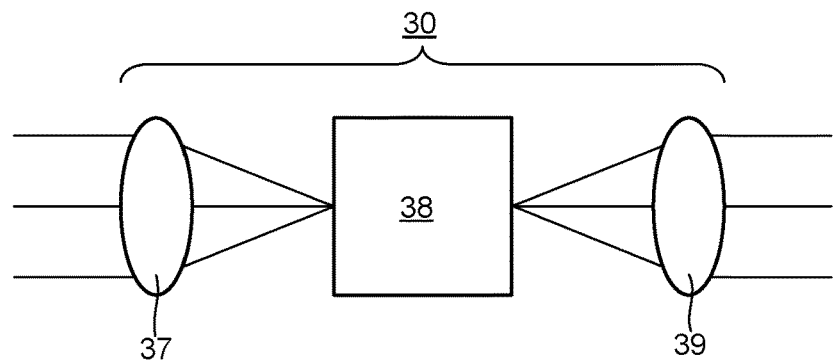
FIG. 5 is a schematic diagram of a beam processing apparatus.
Figure 6:
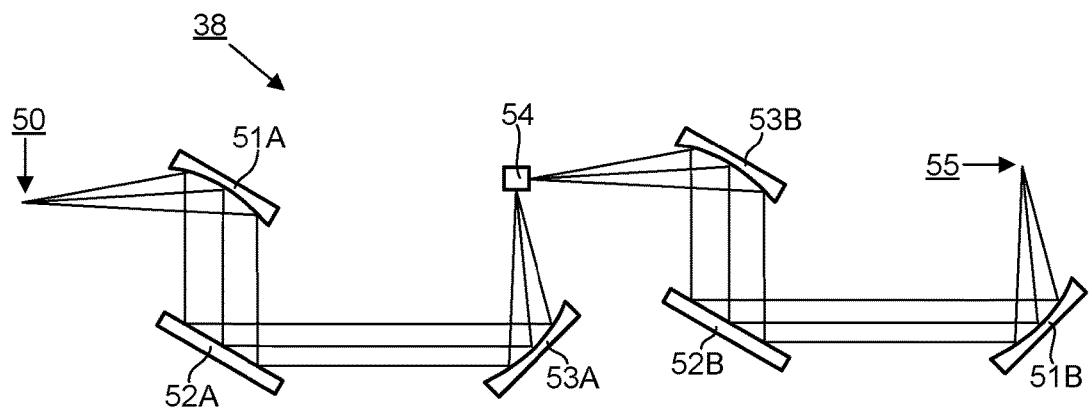
FIG. 6 is a schematic diagram of an example modulating optical system.
Figure 7:
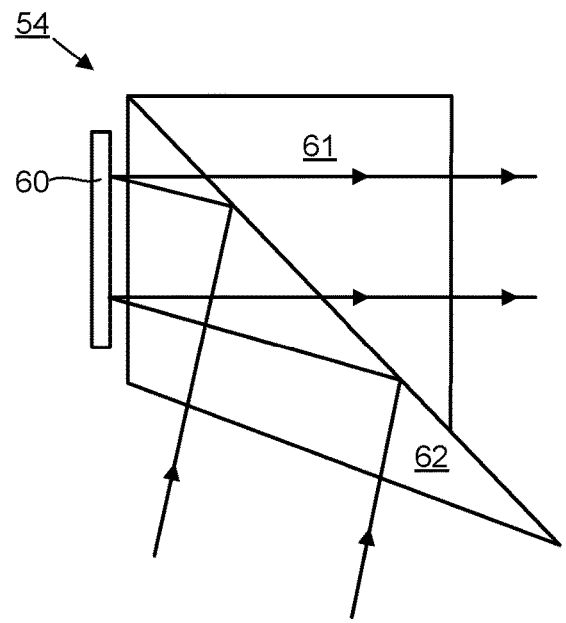
FIG. 7 is a schematic diagram of a modulator and beam separation sub-system for use with the modulating optical system of FIG. 6.
Figure 8:
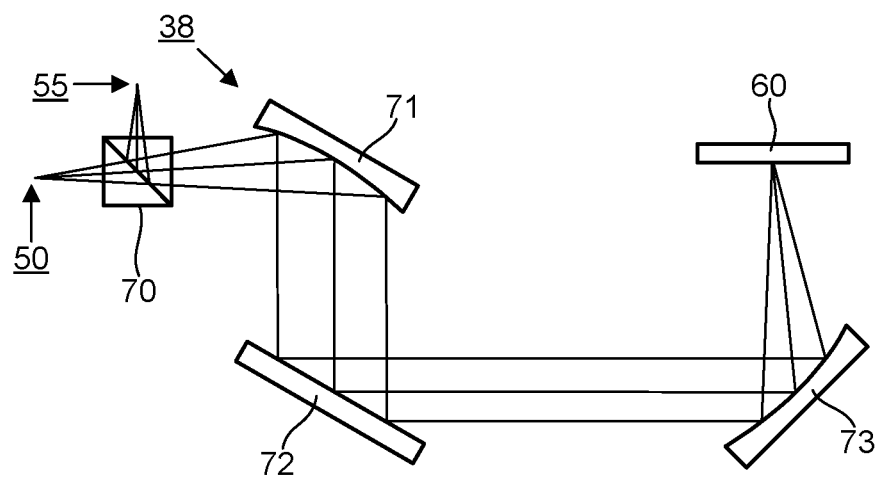
FIG. 8 is a schematic diagram of a further example modulating optical system.

In various embodiments, an example which is depicted schematically in FIG. 5, the beam processing apparatus 30 is configured to operate with an input radiation beam provided in collimated form and is configured to provide an output radiation beam in collimated form. In such embodiments optics 37,39 may be provided to focus the collimated input beam onto an input element or aperture of a modulating optical system 38 (in the example shown, this is achieved using a lens 37). The optics 37,39 are further configured to receive radiation diverging from an output element or output aperture of the modulating optical system 38 and form the collimated output beam (in the example shown, this is achieved using a lens 39). FIGS. 6-8 depict example configurations for the modulating optical system 38.

In various embodiments, the beam processing apparatus 30 comprises an optical system that splits the input radiation beam into a plurality of components. The plurality of components are directed onto a modulator 60. The modulator 60 applies a modulation to at least one of the components independently of at least one other of the components. In various embodiments the modulation is a modulation in time (i.e. a modulation comprising a time varying component of a property such as amplitude or phase). In various embodiments the optical system then recombines the components output from the modulator 60 to form the output radiation beam. Thus, one or more components of the input radiation beam are modulated independently of each other while the components are split apart from each other. Recombining the components into a single beam provides an output radiation beam which comprises one or more independently modulated components in a single beam. The independently modulated components can have different characteristics from each other, such as different wavelengths or different polarization states. The detection system 34 can use the different modulations to distinguish between signals originating from the different components. For example, where a component is amplitude modulated at a particular frequency, phase sensitive detection (also known as synchronous detection) based on the frequency of the modulation can be used to extract a portion of the signal output from the sensor 23 that is modulated at the same frequency. Where plural components are amplitude modulated at different frequencies, phase sensitive detection (synchronous detection) can be used independently to extract respective plural portions of the signal output from the sensor 23.

In various embodiments the detection system 34 comprises a sensor 23 having a response speed capable of registering the modulation applied to each component or each group of components by the modulator 60 (e.g. a response speed that is sufficiently high). For example, where the modulation is registered digitally, the Nyquist-Shannon sampling theorem may be used to determine a minimum sampling speed needed to avoid artifacts. Where analog filters are used, the filters will need to be tuned so that they match the frequency of the modulation. Where phase sensitive detection (synchronous detection) is used, the sensor 23 of the detection system 34 needs to be able to support the phase sensitive detection. In an embodiment, the sensor 23 comprises a fast CCD camera. CCD cameras having frame speeds up to 10 kHz are available for example. In other embodiments a camera with internal synchronous detection is used. Such cameras are able themselves to tune to selected amplitude modulation frequencies of input radiation. In other embodiments, an assembly of optical fibers is used. An example of such an arrangement is depicted schematically in FIG. 11. Ends of the optical fibers 110 (at the lower extremity of FIG. 11) are arranged in a 2D array in the image plane. Each optical fiber end corresponds to a pixel of the sensor 23. Radiation received by each optical fiber 110 (which forms part of the radiation received by the detection system 34) is conveyed by the optical fiber (shown schematically for one optical fiber 110 by dot chain line 114) to a corresponding one of a plurality of individual sensor units 112 (e.g. high speed detectors). This arrangement provides more space for the sensor units 112 than would be possible if the sensor units 112 were positioned at the image plane.

The modulation of components in the output radiation beam allows different contributions to a radiation pattern detected by the sensor 23 to be distinguished from each other even when the contributions overlap spatially within the final radiation pattern. It is not necessary for example for contributions from different wavelength bands to be spatially separated from each other at the sensor 23 for the contributions from the different wavelength bands to be distinguishable from each other. High spatial resolution hyperspectral measurements can thereby be obtained more easily.

Where different wavelength bands are modulated differently, it is possible simultaneously to measure a structure from which the output radiation beam from the beam processing apparatus has been scattered for a plurality of different wavelength bands. High quality measurements of the structure can therefore be made because the measurements are not restricting to a single wavelength band. The measurement may be made with high efficiency because it is not necessary to perform measurements using different wavelength bands at different times.

The use of phase sensitive detection (synchronous detection) further helps to reject noise contributions to the signal and thereby improve signal to noise. Phase sensitive detection (synchronous detection) is known to suppress both static and dynamic noise sources (e.g. 1/f noise reduction).

Cross-talk between radiation bands which are used for different measurements can be reduced. For example, it is common to use radiation in particular bands to perform focus measurements or alignment measurements that are separate from sensing of the target itself. For example, focus measurements may be performed using radiation at a wavelength in the range of 600-700 nm (with bandwidth from 10-50 nm for example) and at a wavelength in range of 750-800 nm (with bandwidth from 10-50 nm for example). Embodiments allow radiation for different measurement purposes to be modulated differently, thereby reducing unwanted cross-talk between the different measurements.

In an embodiment, examples of which are shown in FIGS. 6-8, and discussed with reference to FIGS. 9 and 10, the optical system that splits the input radiation into a plurality of components directs the plurality of components onto a plurality of different regions on the modulator 60. The modulation can then be selected for each component as a function of the region of the modulator onto which the component is incident. In an embodiment, the modulator 60 comprises a spatial light modulator (SLM) comprising an array of programmable elements. In an embodiment the elements are mirrors and the SLM is referred to as a programmable mirror array (described above) or digital mirror device (DMD). Other SLMs are also available, including SLMs based on LC cells and LCOS devices, which are well known in the art of digital projection. Each of the regions on the modulator 60 may contain one or a group of the programmable elements. The programmable elements can thus be used to provide the independent modulation to each of the regions. The modulation may comprise amplitude modulation, for example.

The independent modulation of different components may take various forms. For example, the modulator 60 may modulate a first component differently from a second component (e.g. amplitude modulate the first component at a first frequency and amplitude modulate the second component at a second frequency). Alternatively or additionally, the modulator 60 may modulate a first component and not modulate a second component.

In an embodiment, the optical system that splits the input radiation beam into a plurality of components is such that at least one of the components produced by splitting the input radiation beam comprises radiation in a different wavelength band compared to at least one other of the components produced by splitting the input radiation beam. The different wavelength bands of the different components may overlap with each other or not. The different wavelength bands may comprise discrete wavelength bands that are separated from all other wavelength bands or the different wavelength bands may together form a continuous spread of wavelengths.

In an embodiment, examples of which are shown in FIGS. 6 and 8, the optical system comprises a dispersive element 52A,72. The dispersive element 52A,72 may comprise any element which is capable of changing a direction of propagation of a beam of radiation in a manner that is dependent on the wavelength of the radiation. The dispersive element 52A,72 provides the splitting of the input radiation beam. The dispersive element 52A,72 may comprise for example a diffraction grating or a prism with dispersive glass.

The modulator 60 may modulate the different wavelength bands in various ways. In an embodiment different modulations are applied to each of plurality of different wavelength bands of radiation. In an embodiment, two or more of the different wavelength bands overlap with each other. In another embodiment, none of the different wavelength bands overlap with each other. FIGS. 9 and 10 illustrate some non-limiting possibilities.

Figure 9:
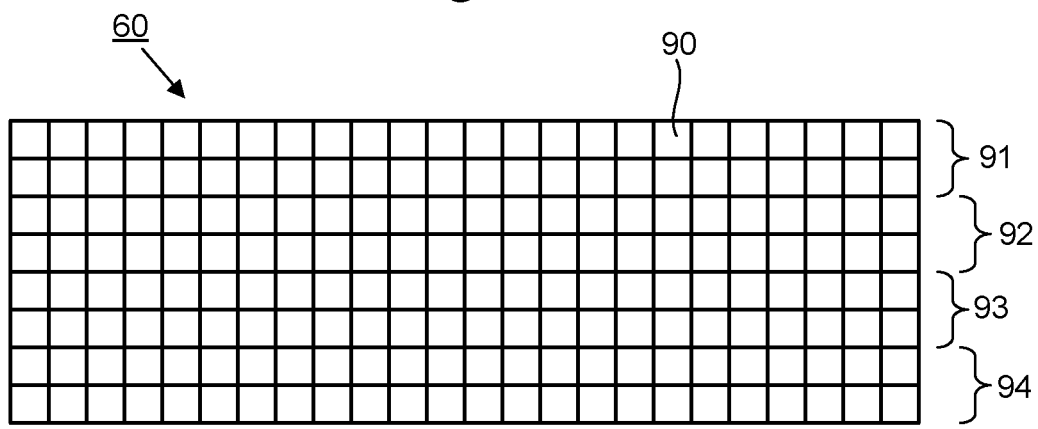
FIG. 9 depicts an array of programmable elements of a modulator.

FIG. 9 depicts an array of programmable elements 90 of a modulator 60. FIG. 10 depicts regions 101-104 that are modulated differently relative to each other. A relatively small number of programmable elements 90 are shown for reasons of clarity. It will be understood that practical systems may comprise arrays with larger numbers of programmable elements 90. A broadband radiation source 11 is provided and the optical system of the beam processing apparatus 30 spreads the input radiation beam across the surface of the modulator 60 according to the wavelength of the radiation, from left to right across the array in the orientation of FIGS. 9 and 10. This may be achieved for example using a diffraction grating or prism. Each element 90 in the same row of the array receives radiation within a different wavelength band relative to all of the other elements in the row. Each element 90 in the same column receives radiation within the same wavelength band as all other elements 90 in the column.

Many different kinds of modulation can be applied using different combinations of the programmable elements 90. In the example of FIGS. 9 and 10, the array of programmable elements 90 is split into four different groups of elements 91-94: 1) rows 1 and 2 (91); rows 3 and 4 (92); rows 5 and 6 (93); and rows 7 and 8 (94).

Figure 10:
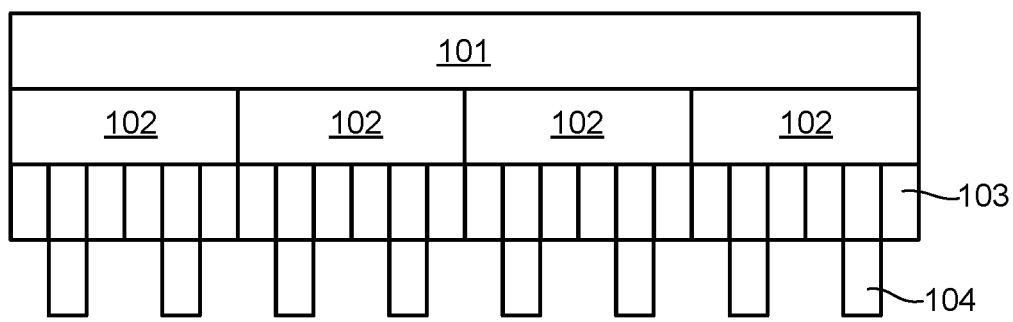
FIG. 10 depicts differently modulated regions on the array of FIG. 9.

Rows 1 and 2 (91) are formed into a single region 101 spanning all of range of wavelengths incident on the portion of the modulator 60 shown in FIGS. 9 and 10. The single region 101 is modulated differently to all of the other regions on the modulator 60. The modulation can be used to extract a portion of the signal output from the sensor 23 that results from relatively broadband scattering from the target.

Rows 3 and 4 (92) are divided into four regions 102. Each of the four regions 102 is modulated differently from each of the other regions 102 and from all other regions on the modulator 60. The modulations in regions 102 can be used to extract portions of the signal output from the sensor 23 that result from scattering from different non-overlapping wavelength bands of radiation. The wavelength bands corresponding to regions 102 do not overlap with each other but do overlap with the broader wavelength band sampled by the wider region 101 of rows 1 and 2.

Rows 5 and 6 (93) are divided into 24 regions 103. In this example, each of the 24 regions 103 is modulated differently from each of the other regions 103 and from all other regions on the modulator 60. In other embodiments, two or more of the regions 103 may have the same modulation. The modulations in regions 103 can be used to extract portions of the signal output from the sensor 23 that result from scattering from different non-overlapping wavelength bands of radiation. The different non-overlapping wavelength bands of radiation sampled by the regions 103 are narrower than the different non-overlapping wavelength bands of radiation sampled by the regions 102 and thereby provide higher spectral resolution.

The regions 102 and the regions 103 allow different modulations to be applied to a plurality of different wavelength bands that together form a continuous spectrum. This is not essential, however, as exemplified by the arrangement of rows 7 and 8.

Rows 7 and 8 (94) are divided into eight regions 104 that are each separated from each other in the horizontal direction. In this example, each of the eight regions 104 is modulated differently from each of the other regions 104 and from all other regions on the modulator 60. In other embodiments, two or more of the regions 104 may have the same modulation. The modulations in regions 104 can be used to extract portions of the signal output from the sensor 23 that result from scattering from different non-overlapping wavelength bands of radiation that are each separated from each other.

The highly flexible modulation of the input radiation beam allows correspondingly flexible measurements to be made using different wavelength bands. The bandwidth can be varied as desired. Overlapping bands can be measured at the same time. Measurements which require relatively broadband radiation can be made at the same time as measurements which require narrower bands or multi-color bands, with no or minimal interference (or cross-talk) between the measurements. The maximum number of wavelength bands (colors) that can be measured simultaneously depends on the integration (measurement) time: if t is the total measurement time per mark the necessary bandwidth is approximately $\Delta f=3/t$, such that for t=15 ms $\Delta f$=200 Hz.

FIGS. 6 and 7, and FIG. 8, depict example modulating optical systems 38 for achieving the splitting, independent modulating, and recombination of the radiation beam. Both modulating optical systems 38 use sequences of components that resemble those usable for a standard monochromator, but are used here to direct different wavelength components of the input radiation beam onto different regions of the modulator rather than to filter out unwanted wavelength components. As will be described in further detail below, in the embodiment of FIGS. 6 and 7, two such monochromator-style arrangements are provided in a back to back arrangement. In the embodiment of FIG. 8, a single monochromator-style arrangement is provided that is traversed twice by the radiation being processed by the modulating optical system 38.

In an embodiment, the optical system is such that a first optical path is adopted by radiation propagating from a first focus 50 to the modulator 60. A second optical path is adopted by radiation propagating from the modulator 60 to a second focus 55.

In various embodiments, a geometry of the first optical path is identical to, or mirror symmetric with respect to, a geometry of the second optical path, at least for portions of the first optical path in which the radiation is not in a collimated form, for each of a plurality of different wavelengths. This principle provides a simple and reliable way to ensure that the splitting apart of the different components in the first optical path is exactly reversed in the second optical path, thereby providing the recombined output radiation beam. Optionally, the path length of the first optical path is substantially the same as the path length of the second optical path, for each of a plurality of different wavelengths.

In the example of FIGS. 6 and 7, radiation is directed from the first focus 50 onto a dispersive element 52A via a mirror 51A. The dispersive element 52A may be a reflective diffraction grating for example. Radiation is directed from the dispersive element 52A along different paths (as a function of the wavelength of the radiation) onto a modulator and beam separation sub-system 54 via mirror 53A. The modulator and beam separation sub-system 54 comprises the modulator 60 and optics for separating incoming and outgoing radiation to/from the modulator 60.

FIG. 7 depicts an example configuration for the modulator and beam separation sub-system 54 suitable for the modulating optical system 38 of FIG. 6. In this particular embodiment, the modulator and beam separation sub-system 54 comprises a modulator 60 (e.g. array of programmable elements, such as a DMD) and a TIR (total internal reflection) prism (a combination of two prisms 61,62 in the example shown). TIR prisms are known for use in separating incoming and outgoing beams to/from arrays of programmable elements such as DMDs, for example in the context of digital projectors using DMDs.

FIG. 6 is an example of embodiments in which additional components that are optically identical to a plurality of optical elements in the first optical path are provided in the second optical path and configured such that a geometry of the first optical path is identical to, or mirror symmetric with respect to, a geometry of the second optical path, at least for portions of the first optical path in which the radiation is not in a collimated form, for each of the plurality of different wavelengths. In this particular example, the additional components are also configured such that the path length of the first optical path is substantially the same as the path length of the second optical path for each of the plurality of different wavelengths. In the example of FIG. 6, optical elements 51A, 52A and 53A in the first optical path have (optically identical) equivalents 51B, 52B and 53B in the second optical path that are encountered in the reverse order elements 51B, 52B and 53B are therefore examples of the additional components mentioned above. Radiation thus diverges from the first focus 50 to mirror 51A, is split by the dispersive element 52A, is modulated by the modulator 60, recombined by the dispersive element 52B, and is focused again by the mirror 51B at the second focus 55. The geometry of the optical path for each different wavelength from element 51A to element 54 is identical to, or mirror symmetric with respect to, the geometry of the optical path for each different wavelength from element 51B to element 54.

FIG. 8 depicts an example of an alternative embodiment in which a plurality of optical elements are common to the first optical path and the second optical path, with the first optical path being the exact reverse of the second optical path for at least a portion of the first optical path and the second optical path. Thus, radiation diverges from the first focus 50 to mirror 71, is split by dispersive element 72, is directed onto the modulator by mirror 73, is modulated by the modulator 60, is directed back onto the dispersive element 72 by mirror 73, is recombined by the dispersive element 72, and is focused again by the mirror 71 at the second focus 55. Radiation entering the modulating optical system 38 from the first focus 50 is separated from radiation leaving the modulating optical system 38 via the second focus 55 by a beam splitter 70. The beam splitter 70 may for example be a non-polarizing beam splitter (NPBS). The arrangement of FIG. 8 can desirably be implemented using fewer components that the arrangement of FIGS. 6 and 7 and can be made more compact.

In the above embodiments, the input radiation beam is split in order to apply different modulations to different wavelength bands. In other embodiments, alternatively or additionally, at least one of the components produced by splitting the input radiation beam has a different polarization state compared to at least one other of the components produced by splitting the input radiation beam. In such embodiments, different modulations can be applied to different polarization components.

The measurement system 30 may be used as a metrology apparatus in a lithographic system. In an embodiment, a lithographic apparatus for performing a lithographic process uses the result of a measurement by the measurement system of a structure formed by the lithographic process, for example when performing a subsequent lithographic process.

The concepts described herein can be used to enable parallel readout of a multispectral measurement instead of having to select each wavelength separately and perform multiple measurements in series. Such measurements may be used, for example, in performing overlay measurements on overlay targets.

Having parallel measurements with different wavelengths make the measurements more robust. For example, better asymmetry correction can be obtained by combining multiple colors (e.g. by using blind source separation techniques).

The concepts disclosed herein may find utility beyond post-lithography measurement of structures for monitoring purposes. For example, such a detector architecture may be used in future alignment sensor concepts that are based on pupil plane detection, used in lithographic apparatuses for aligning the substrate during the patterning process.

While the targets described above are metrology targets specifically designed and formed for the purposes of measurement, in other embodiments, properties may be measured on targets which are functional parts of devices formed on the substrate. Many devices have regular, grating-like structures. The terms 'target grating' and 'target' as used herein do not require that the structure has been provided specifically for the measurement being performed.

The metrology apparatus can be used in a lithographic system, such as the lithographic cell LC discussed above with reference to FIG. 2. The lithographic system comprises a lithographic apparatus LA that performs a lithographic process. The lithographic apparatus may be configured to use the result of a measurement by the metrology apparatus of a structure formed by the lithographic process, for example when performing a subsequently lithographic process, for example to improve the subsequent lithographic process.

An embodiment may include a computer program containing one or more sequences of machine-readable instructions describing methods of measuring targets on a structures and/or analyzing measurements to obtain information about a lithographic process. There may also be provided a data storage medium (e.g., semiconductor memory, magnetic or optical disk) having such a computer program stored therein. Where an existing lithography or metrology apparatus is already in production and/or in use, the invention can be implemented by the provision of updated computer program products for causing a processor to perform the methods described herein.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

Further embodiments according to the invention are further described in below numbered clauses:

1. A measurement system comprising:
a first optical system configured to split an input radiation beam into a plurality of components;
a modulator configured to receive the plurality of components and apply a modulation to at least one of the components independently of at least one other of the components; and
a second optical system configured to illuminate a target with the plurality of components and direct radiation scattered by the target to a detection system, wherein:
the detection system is configured to distinguish between each of one or more components, or between each of one or more groups of components, of the radiation directed to the detection system based on the modulation applied to each component or each group of components by the modulator.

2. The system of clause 1, wherein:
the first optical system is further configured to recombine the components output from the modulator to form an output radiation beam; and
the illuminating of the target with the plurality of the components comprises illuminated the target with said output radiation beam.

3. The system of clause 1 or 2, wherein the detection system is configured to perform the distinguishing between each of one or more components, or between each of one or more groups of components, using phase sensitive detection based on a frequency of the modulation applied to each component or each group of components by the modulator.

4. The system of any preceding clause, wherein the detection system comprises a sensor having a response speed capable of registering the modulation applied to each component or each group of components by the modulator.

5. The system of clause 4, wherein the sensor comprises a plurality of sensor units and a corresponding plurality of optical fibers, each optical fiber being configured to convey radiation received by the detection system to a respective one of the plurality of sensor units.

6. The system of any preceding clause, wherein:
the first optical system is configured to direct the plurality of components onto a corresponding plurality of different regions on the modulator.

7. The system of clause 6, wherein the modulation is selected for each component as a function of the region of the modulator onto which the component is incident.

8. The system of clause 7, wherein the modulator comprises a spatial light modulator comprising a plurality of individually controllable elements, and each of the regions contains one or a group of the individually controllable elements.

9. The system of any preceding clause, wherein the modulation comprises amplitude modulation.

10. The system of any preceding clause, wherein the modulator is configured to modulate a first component differently to a second component or to modulate a first component and not modulate a second component.

11. The system of any preceding clause, wherein the first optical system is configured such that at least one of the components produced by splitting the input radiation beam comprises radiation in a different wavelength band compared to at least one other of the components produced by splitting the input radiation beam.

12. The system of any preceding clause, wherein the first optical system comprises a dispersive element configured to re-direct radiation as a function of the wavelength of the radiation and thereby provide the splitting of the input radiation beam.

13. The system of clause 12, wherein the dispersive element comprises a diffraction grating or prism.

14. The system of any of clauses 11-13, configured to apply a modulation of different frequency to each of a plurality of different wavelength bands of radiation.
15. The system of clause 14, wherein two or more of the different wavelength bands overlap with each other.
16. The system of clause 14, wherein none of the different wavelength bands overlap with each other.
17. The system of any preceding clause, wherein the first optical system is configured such that at least one of the components produced by splitting the input radiation beam has a different polarization state compared to at least one other of the components produced by splitting the input radiation beam.
18. The system of clause 17, configured to apply a modulation of different frequency to each of a plurality of different polarization components of the input radiation beam.
19. The system of any preceding clause, wherein:
the first optical system is such that a first optical path is adopted by radiation propagating from a first focus to the modulator and a second optical path is adopted by radiation propagating from the modulator to a second focus.
20. The system of clause 19, wherein a geometry of the first optical path is identical to, or mirror symmetric with respect to, a geometry of the second optical path, at least for portions of the first optical path in which the radiation is not in a collimated form, for each of a plurality of different wavelengths.
21. The system of clause 19 or 20, wherein the path length of the first optical path is substantially the same as the path length of the second optical path, for each of a plurality of different wavelengths.
22. The system of any of clauses 19-21, wherein a plurality of optical elements are common to the first optical path and the second optical path, with the first optical path being the exact reverse of the second optical path for at least a portion of the first optical path and the second optical path, for each of a plurality of different wavelengths.
23. The system of any of clauses 19-22, wherein additional components that are optically identical to a plurality of optical elements in the first optical path are provided in the second optical path, the additional components being configured such that a geometry of the first optical path is identical to, or mirror symmetric with respect to, a geometry of the second optical path, at least for portions of the first optical path in which the radiation is not in a collimated form, for each of the plurality of different wavelengths.
24. The system of any preceding clause, wherein the input radiation beam is collimated and the output radiation beam is collimated.
25. The system of any preceding clause, wherein the modulation comprises a modulation in time.
26. The system of any preceding clause, wherein the target is a structure formed by a lithographic apparatus.
27. A lithographic system comprising:
a lithographic apparatus configured to perform a lithographic process; and
the system of any preceding clause, wherein:
the lithographic apparatus is arranged to use the result of a measurement by the measurement system of a structure formed by the lithographic process.
28. A method of measuring a target, comprising:
splitting an input radiation beam into a plurality of components;
applying a modulation to at least one of the components independently of at least one other of the components;
illuminating a target with the plurality of components;
detecting radiation scattered by the target; and
distinguishing between each of one or more components, or between each of one or more groups of components, of the radiation scattered by the target based on the modulation applied to each component or each group of components.
29. The method of clause 28, wherein:
the plurality of components are recombined into a single output radiation beam after the modulation; and
the illuminating of the target with the plurality of the components comprises illuminated the target with said output radiation beam.
30. The method of clause 28 or 29, wherein the distinguishing between each of one or more components, or between each of one or more groups of components, is performed using phase sensitive detection based on a frequency of the modulation applied to each component or each group of components.
31. The method of any of clauses 28-30, wherein the detecting of the radiation scattered by the target is performed using a detection system having a response speed capable of registering the modulation applied to each component or each group of components.
32. The method of clause 31, wherein the detection system comprises a plurality of sensor units and a corresponding plurality of optical fibers, each optical fiber conveying radiation received by the detection system to a respective one of the plurality of sensor units.
33. The method of any of clauses 28-32, wherein:
the modulations are applied by directing the plurality of components onto a corresponding plurality of different regions on a modulator.
34. The method of clause 33, wherein the modulation is selected for each component as a function of the region of the modulator onto which the component is incident.
35. The method of clause 34, wherein the modulator comprises a spatial light modulator comprising a plurality of individually controllable elements, and each of the regions contains one or a group of the individually controllable elements.
36. The method of any of clauses 28-35, wherein the modulation comprises amplitude modulation.
37. The method of any of clauses 28-36, wherein the modulator modulates a first component differently to a second component or modulates a first component and does not modulate a second component.
38. The method of any of clauses 28-37, wherein at least one of the components produced by splitting the input radiation beam comprises radiation in a different wavelength band compared to at least one other of the components produced by splitting the input radiation beam.
39. The method of any of clauses 28-38, wherein a dispersive element is used to re-direct radiation as a function of the wavelength of the radiation and thereby provide the splitting of the input radiation beam.
40. The method of clause 39, wherein the dispersive element comprises a diffraction grating or prism.
41. The method of any of clauses 38-40, wherein a modulation of different frequency is applied to each of a plurality of different wavelength bands of radiation.
42. The method of clause 41, wherein two or more of the different wavelength bands overlap with each other.
43. The method of clause 41, wherein none of the different wavelength bands overlap with each other.
44. The method of any of clauses 28-43, wherein at least one of the components produced by splitting the input radiation beam has a different polarization state compared to at least one other of the components produced by splitting the input radiation beam.

45. The method of clause 44, wherein a modulation of different frequency is applied to each of a plurality of different polarization components of the input radiation beam.

46. The method of any of clauses 28-35, wherein the input radiation beam is collimated and the output radiation beam is collimated.

47. The method of any of clauses 28-46, wherein the modulation comprises a modulation in time.

48. The method of any of clauses 28-47, wherein the target is a structure formed by a lithographic apparatus.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A measurement system comprising:
a first optical system comprising a dispersive element configured to split an input radiation beam into a plurality of components;
a modulator configured to receive the plurality of components and apply a modulation to a first component independently of a second component of the plurality of components; and
a second optical system comprising a beam splitter configured to direct the components to illuminate a target and direct radiation scattered by the target to a detection system, wherein the detection system is configured to distinguish between the components or between groups of the components of the radiation directed to the detection system based on the modulation applied to the first and second components or the groups of components by the modulator.

2. The measurement system of claim 1, wherein:
the first optical system is further configured to recombine the components output from the modulator to form an output radiation beam; and
the second optical system is configured to illuminate the target with the output radiation beam.

3. The measurement system of claim 1, wherein the detection system is configured to perform the distinguishing between the components or between the groups of the components using phase sensitive detection based on a frequency of the modulation applied to the components or the groups of the components by the modulator.

4. The measurement system of claim 1, wherein the detection system comprises a sensor having a response speed capable of registering the modulation applied to the components or the groups of the components by the modulator.

5. The measurement system of claim 4, wherein the sensor comprises a plurality of sensor units and a corresponding plurality of optical fibers, each of the plurality of optical fibers being configured to convey radiation received by the detection system to a respective one of the plurality of sensor units.

6. The measurement system of claim 1, wherein:
the first optical system is configured to direct the components onto a corresponding plurality of different regions on the modulator.

7. The measurement system of claim 6, wherein the modulation is selected for respective ones of the components as a function of the region of the modulator onto which the respective ones of the components is incident.

8. The measurement system of claim 7, wherein:
the modulator comprises a spatial light modulator comprising individually controllable elements, and
the regions contain one or a group of the individually controllable elements.

9. The measurement system of claim 1, wherein the first optical system is configured such that the first one of the components produced by splitting the input radiation beam comprises radiation in a different wavelength band compared to the second one of the components produced by splitting the input radiation beam.

10. The measurement system of claim 1, wherein the dispersive element is configured to re-direct radiation as a function of the wavelength of the radiation and thereby provide the splitting of the input radiation beam.

11. The measurement system claim 1, wherein the first optical system is configured such the first one of the components produced by splitting the input radiation beam has a different polarization state compared to the second one of the components produced by splitting the input radiation beam.

12. The measurement system of claim 11, configured to apply a modulation of different frequency to different polarization components of the input radiation beam.

13. The measurement system of claim 1, wherein:
the first optical system is such that a first optical path is adopted by radiation propagating from a first focus to the modulator and a second optical path is adopted by radiation propagating from the modulator to a second focus.

14. The measurement system of claim 13, wherein a geometry of the first optical path is identical to, or mirror symmetric with respect to, a geometry of the second optical path, at least for portions of the first optical path in which the radiation is not in a collimated form, for each of a plurality of different wavelengths.

15. The measurement system of claim 13, wherein the path length of the first optical path is substantially the same as the path length of the second optical path, for each of a plurality of different wavelengths.

16. The measurement system of claim 13, wherein optical elements are common to the first optical path and the second optical path, with the first optical path being the exact reverse of the second optical path for a portion of the first optical path and the second optical path, for a plurality of different wavelengths.

17. The measurement system of claim 13, wherein additional optical elements that are optically identical to a plurality of optical elements in the first optical path are provided in the second optical path, the additional optical elements being configured such that a geometry of the first optical path is identical to, or mirror symmetric with respect to, a geometry of the second optical path, at least for portions of the first optical path in which the radiation is not in a collimated form, for each of the plurality of different wavelengths.

18. The measurement system of claim 1, wherein the target is a structure formed by a lithographic apparatus.

19. A lithographic system comprising:
   a lithographic apparatus configured to perform a lithographic process; and
   a measurement system comprising:
      a first optical system comprising a dispersive element configured to split an input radiation beam into components;
      a modulator configured to receive the components and apply a modulation to a first component independently of a second component of the plurality of components; and
      a second optical system comprising a beam splitter configured to direct the components to illuminate a target and direct radiation scattered by the target to a detection system, wherein the detection system is configured to distinguish between the components or between groups of the components of the radiation directed to the detection system based on the modulation applied to the first and second components or the groups of components by the modulator;
   wherein the lithographic apparatus is arranged to use the result of a measurement by the measurement system of a structure formed by the lithographic process.

20. A method of measuring a target, comprising:
   splitting an input radiation beam into a plurality of components;
   applying a modulation to a first component independently of a second component of the plurality of components;
   illuminating a target with the components;
   detecting radiation scattered by the target; and
   distinguishing between the components or between groups of the components of the radiation scattered by the target based on the modulation applied to the components or the groups of components using a detection system comprising a sensor having a response speed capable of registering the modulation applied to the components or the groups of the components, wherein the sensor comprises a plurality of sensor units and a corresponding plurality of optical fibers, each of the plurality of optical fibers being configured to convey radiation received by the detection system to a respective one of the plurality of sensor units.

* * * * *